United States Patent
Grossenbacher

(10) Patent No.: US 7,992,424 B1
(45) Date of Patent: Aug. 9, 2011

(54) ANALYTICAL INSTRUMENTATION AND SAMPLE ANALYSIS METHODS

(75) Inventor: John Grossenbacher, Lafayette, IN (US)

(73) Assignee: Griffin Analytical Technologies, L.L.C., West Lafayette, IN (US)

( * ) Notice: Subject to any disclaimer, the term of this patent is extended or adjusted under 35 U.S.C. 154(b) by 676 days.

(21) Appl. No.: 11/900,958

(22) Filed: Sep. 14, 2007

Related U.S. Application Data

(60) Provisional application No. 60/844,896, filed on Sep. 14, 2006.

(51) Int. Cl.
*G01N 1/28* (2006.01)

(52) U.S. Cl. .................................................. 73/23.41

(58) Field of Classification Search .................. None
See application file for complete search history.

(56) References Cited

U.S. PATENT DOCUMENTS

| | | |
|---|---|---|
| 3,633,173 A | 1/1972 | Edge |
| 3,984,692 A | 10/1976 | Arsenault |
| 3,992,632 A | 11/1976 | Kruger et al. |
| 4,008,388 A | 2/1977 | McLafferty et al. |
| 4,105,916 A | 8/1978 | Siegel |
| 4,388,531 A | 6/1983 | Stafford et al. |
| 4,423,324 A | 12/1983 | Stafford et al. |
| 4,433,982 A | 2/1984 | Odernheimer et al. |
| 4,540,884 A | 9/1985 | Stafford et al. |
| 4,567,897 A | 2/1986 | Endo et al. |
| 4,644,494 A | 2/1987 | Muller |
| 4,755,685 A | 7/1988 | Kawanami et al. |
| 4,757,198 A | 7/1988 | Korte et al. |
| 4,761,545 A | 8/1988 | Marshall et al. |
| 4,766,312 A | 8/1988 | Fergusson et al. |
| 4,771,172 A | 9/1988 | Weber-Grabau et al. |
| 4,791,292 A | 12/1988 | Cooks et al. |
| 4,810,882 A | 3/1989 | Bateman |
| 4,849,628 A | 7/1989 | McLuckey et al. |
| 4,882,484 A | 11/1989 | Franzen et al. |

(Continued)

FOREIGN PATENT DOCUMENTS

DE   4008388   9/1991

(Continued)

OTHER PUBLICATIONS

Ojala, Marja, Novel Membrane Inlet Mass Spectrometic Methods for Analysis of Organic Compounds in Aqueous and Solid Samples, *VTT Publications Technical Research Centre of Finland ESPOO 2001*.

(Continued)

*Primary Examiner* — Daniel S Larkin
(74) *Attorney, Agent, or Firm* — Wells St. John P.S.

(57) ABSTRACT

Sample introduction components of analytical instruments are provided that can include a membrane inlet component in fluid communication with both a mass analyzer component and a sample inlet. The components can also include a valve in fluid communication with the sample inlet and a sampling component. Components can include a sample loop assembly in fluid communication with valve, and a preconcentration assembly in fluid communication with the valve. Sample analysis methods are provided that can include providing sample to a membrane in fluid communication with a mass analyzer to acquire sample parameter data, and providing the sample to a sampling assembly upon acquisition of predefined sample parameter data. Methods can also include providing sample to a first sampling assembly in fluid communication with a detection component to acquire sample parameter data, providing the sample to a second sampling assembly upon acquisition of predefined sample parameter data.

3 Claims, 11 Drawing Sheets

U.S. PATENT DOCUMENTS

| | | | |
|---|---|---|---|
| 4,912,326 A | 3/1990 | Naito | |
| 4,945,236 A | 7/1990 | Mogami et al. | |
| 4,956,788 A | 9/1990 | Sidi et al. | |
| 4,988,867 A | 1/1991 | Laprade | |
| 4,991,428 A * | 2/1991 | Heyde | 73/61.56 |
| 4,996,422 A | 2/1991 | Mitsui et al. | |
| 5,015,848 A | 5/1991 | Bomse et al. | |
| 5,083,021 A | 1/1992 | Devant et al. | |
| 5,083,450 A | 1/1992 | Grindstaff | |
| 5,107,109 A | 4/1992 | Stafford, Jr. et al. | |
| 5,109,691 A * | 5/1992 | Corrigan et al. | 73/23.36 |
| 5,153,433 A | 10/1992 | Andresen et al. | |
| 5,155,357 A | 10/1992 | Hemond | |
| 5,202,561 A | 4/1993 | Giessmann et al. | |
| 5,245,192 A | 9/1993 | Houseman | |
| 5,248,882 A | 9/1993 | Liang | |
| 5,304,799 A | 4/1994 | Kurzweg | |
| 5,313,061 A | 5/1994 | Drew et al. | |
| 5,324,939 A | 6/1994 | Louris et al. | |
| 5,401,965 A | 3/1995 | Kaneko et al. | |
| 5,420,425 A | 5/1995 | Bier et al. | |
| 5,426,300 A | 6/1995 | Voss et al. | |
| 5,436,447 A | 7/1995 | Shew | |
| 5,448,061 A | 9/1995 | Wells | |
| 5,448,062 A | 9/1995 | Cooks et al. | |
| 5,462,660 A * | 10/1995 | Singleton et al. | 210/198.2 |
| 5,479,012 A | 12/1995 | Wells | |
| 5,479,747 A | 1/1996 | Wu | |
| 5,481,107 A | 1/1996 | Takada et al. | |
| 5,509,602 A | 4/1996 | Liu | |
| 5,525,799 A | 6/1996 | Andresen et al. | |
| 5,559,325 A | 9/1996 | Franzen | |
| 5,572,022 A | 11/1996 | Schwartz et al. | |
| 5,686,655 A | 11/1997 | Itoi | |
| 5,696,376 A | 12/1997 | Doroshenko et al. | |
| 5,723,862 A | 3/1998 | Forman | |
| 5,760,785 A | 6/1998 | Barber et al. | |
| 5,773,822 A | 6/1998 | Kitamura et al. | |
| 5,777,205 A | 7/1998 | Nakagawa et al. | |
| 5,789,747 A | 8/1998 | Kato et al. | |
| 5,808,308 A | 9/1998 | Holkeboer | |
| 5,818,055 A | 10/1998 | Franzen | |
| 5,837,883 A | 11/1998 | Itoi | |
| 5,844,237 A | 12/1998 | Whitehouse et al. | |
| 5,852,295 A | 12/1998 | Da Silveira et al. | |
| 5,896,196 A | 4/1999 | Pinnaduwage | |
| 6,025,590 A | 2/2000 | Itoi | |
| 6,133,568 A | 10/2000 | Weiss et al. | |
| 6,165,251 A | 12/2000 | Lemieux et al. | |
| 6,215,146 B1 | 4/2001 | Umeda et al. | |
| 6,235,197 B1 * | 5/2001 | Anderson et al. | 210/635 |
| 6,239,429 B1 | 5/2001 | Blessing et al. | |
| 6,253,162 B1 | 6/2001 | Jarman et al. | |
| 6,287,988 B1 | 9/2001 | Nagamine et al. | |
| 6,329,654 B1 | 12/2001 | Gulcicek et al. | |
| 6,351,983 B1 | 3/2002 | Haas et al. | |
| 6,410,914 B1 | 6/2002 | Park et al. | |
| 6,469,298 B1 | 10/2002 | Ramsey et al. | |
| 6,472,661 B1 | 10/2002 | Tanaka et al. | |
| 6,472,684 B1 | 10/2002 | Yamazaki et al. | |
| 6,476,537 B1 | 11/2002 | Pease et al. | |
| 6,487,523 B2 | 11/2002 | Jarman et al. | |
| 6,489,649 B2 | 12/2002 | Kobayashi et al. | |
| 6,496,905 B1 | 12/2002 | Yoshioka et al. | |
| 6,509,602 B2 | 1/2003 | Yamazaki et al. | |
| 6,530,563 B1 | 3/2003 | Miller et al. | |
| 6,541,765 B1 | 4/2003 | Vestal | |
| 6,541,768 B2 | 4/2003 | Andrien et al. | |
| 6,549,861 B1 | 4/2003 | Mark et al. | |
| 6,559,443 B2 | 5/2003 | Shiokawa et al. | |
| 6,570,151 B1 | 5/2003 | Grosshans et al. | |
| 6,577,531 B2 | 6/2003 | Kato | |
| 6,586,727 B2 | 7/2003 | Bateman et al. | |
| 6,593,568 B1 | 7/2003 | Whitehouse et al. | |
| 6,593,585 B1 | 7/2003 | Kobayashi et al. | |
| 6,596,585 B2 | 7/2003 | Kobayashi et al. | |
| 6,596,989 B2 | 7/2003 | Kato | |
| 6,621,077 B1 | 9/2003 | Guevremont et al. | |
| 6,646,254 B2 | 11/2003 | Tanaka | |
| 6,649,129 B1 | 11/2003 | Neal | |
| 6,677,582 B2 | 1/2004 | Yamada et al. | |
| 6,679,093 B2 | 1/2004 | Johnson et al. | |
| 6,686,592 B1 | 2/2004 | Sakairi et al. | |
| 6,710,336 B2 | 3/2004 | Wells | |
| 6,717,130 B2 | 4/2004 | Bateman et al. | |
| 6,737,644 B2 | 5/2004 | Itoi | |
| 6,744,045 B2 | 6/2004 | Fries et al. | |
| 6,750,449 B2 | 6/2004 | Marcus | |
| 6,753,523 B1 | 6/2004 | Whitehouse et al. | |
| 6,756,640 B2 | 6/2004 | Yamazaki et al. | |
| 6,759,652 B2 | 7/2004 | Yoshinari et al. | |
| 6,759,706 B2 | 7/2004 | Kobayashi | |
| 6,762,406 B2 | 7/2004 | Cooks et al. | |
| 6,764,902 B2 | 7/2004 | Kobayashi et al. | |
| 6,815,673 B2 | 11/2004 | Plomley et al. | |
| 6,825,466 B2 | 11/2004 | Mordekhay | |
| 6,835,927 B2 | 12/2004 | Becker et al. | |
| 6,861,650 B2 | 3/2005 | Kondo et al. | |
| 6,902,937 B2 * | 6/2005 | Vanatta | 436/101 |
| 6,906,322 B2 | 6/2005 | Berggren et al. | |
| 6,939,718 B2 | 9/2005 | Singh et al. | |
| 7,015,466 B2 | 3/2006 | Takats et al. | |
| 7,026,177 B2 | 4/2006 | Laprade | |
| 7,045,776 B2 | 5/2006 | Kaufman et al. | |
| 7,047,144 B2 | 5/2006 | Steiner | |
| 7,129,481 B2 | 10/2006 | Overney | |
| 7,138,626 B1 | 11/2006 | Karpetsky | |
| 7,230,601 B2 | 6/2007 | Yamazaki et al. | |
| 7,294,832 B2 | 11/2007 | Wells et al. | |
| 7,339,820 B2 | 3/2008 | Kato | |
| 7,355,169 B2 | 4/2008 | McLuckey et al. | |
| 7,388,197 B2 | 6/2008 | McLean et al. | |
| 7,427,750 B2 | 9/2008 | Grossenbacher et al. | |
| 7,439,121 B2 | 10/2008 | Ohmi et al. | |
| 7,449,170 B2 | 11/2008 | Regnier et al. | |
| 7,462,821 B2 | 12/2008 | Barket, Jr. et al. | |
| 2002/0005479 A1 | 1/2002 | Yoshinari et al. | |
| 2002/0113268 A1 | 8/2002 | Koyama et al. | |
| 2002/0195556 A1 | 12/2002 | Yoshinari et al. | |
| 2003/0037589 A1 * | 2/2003 | Johnson et al. | 73/1.02 |
| 2003/0113936 A1 | 6/2003 | Yamamoto | |
| 2006/0043023 A1 * | 3/2006 | Srinivasan et al. | 210/659 |
| 2006/0231769 A1 | 10/2006 | Stresau et al. | |
| 2006/0255258 A1 | 11/2006 | Wang et al. | |
| 2007/0162232 A1 | 7/2007 | Patterson et al. | |
| 2007/0213940 A1 | 9/2007 | Rardin et al. | |
| 2007/0266858 A1 * | 11/2007 | Alm et al. | 96/105 |

FOREIGN PATENT DOCUMENTS

| | | |
|---|---|---|
| EP | 0 336 990 A1 | 10/1989 |
| GB | 2 026 231 | 8/1979 |
| GB | 2 363 249 A | 12/2001 |
| GB | 2 406 434 A | 3/2005 |
| JP | 63318061 | 12/1988 |
| JP | 11 073911 A | 3/1999 |
| JP | 2000314724 | 11/2000 |
| WO | WO 01/93307 | 12/2001 |
| WO | WO 04/097352 | 11/2004 |

OTHER PUBLICATIONS

Camel, V. and Caude, M., Trace Enrichment Methods for the Determination of Organic Pollutants in Ambient Air, *J. Chrom. A.*, 710 (1995) p. 3-19.

Badman, Ethan R., and Coks, R. Graham, "Cylindrical Ion Trap Array with Mass Selection by Variation in Trap Dimensions" Anal. Chem. 2000, 72, pp. 5079-5096.

Barlow, et al., "Determination of Analytic Potentials from Finite Element Computations" Int. Journal of Mass Spectrometry, Apr. 12, 2001, pp. 19-29.

Bollen et al., "Isoltrap: A Tandem Penning Trap System for Accurate On-line Mass Determination of Short-lived Isotopes" Nuclear Instruments & Methods in Physics Research, Jan. 11, 1996, pp. 675-697.

Carroll et al.; "A Dual Vacuum chamber Fourier Transform Mass Spectrometer with Rapidly Interchangeable Lsims and Maldi" Analytical Chemistry vol. 78 No. 10, May 15, 1996.

Groves, David. "Field Portable Ms for Explosive Detection" 4th Harsh Environments Spectrometry Workshop, Oct. 9, 2003, all slides.

Johnson et al.; "Membrane Introduction Mass Spectrometry: Trends and Applications" Mass Spectrometry Reviews (2000) 19, pp. 1-37.

Louris et al., "Instrumentation, Applications, and Energy Deposition in Quadrupole Ion-Trap Tandem Mass Spectrometry" Anal. Chem., 1987, 59, pp. 1677-1685.

McLuckey et al.; "High Explosives Vapor Detection by Glow Discharge - Ion Trap Mass Spectrometry" Rapid Communications in Mass Spectrometry vol. 10 (1996) pp. 287-298.

Schwartz et al., "A Two -Dimensional Quadropole Ion Trap Mass Spectrometer" American Society for Mass Spectrometry 2002, pp. 659-669.

Vestal, Marvin L.; "Methods of Ion Generation" Chem. Rev. 2001, 101(2); pp. 361-375.

Wells, et al., "A Quadrupole Ion Trap with Cylindrical Geometry Operated in the Mass-Selective Instability Mode" Anal. Chem., 1998, 70, pp. 438-444.

\* cited by examiner

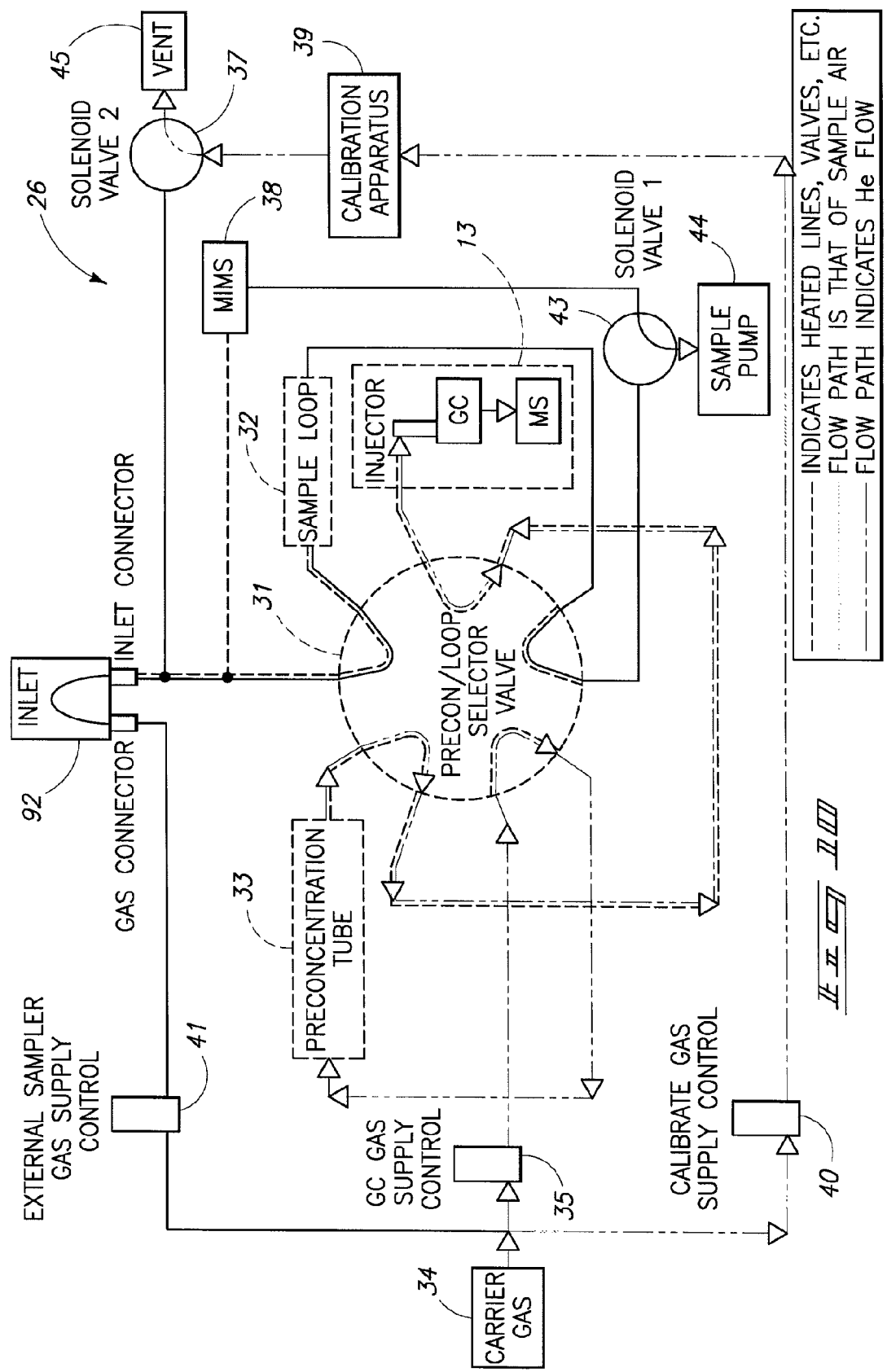

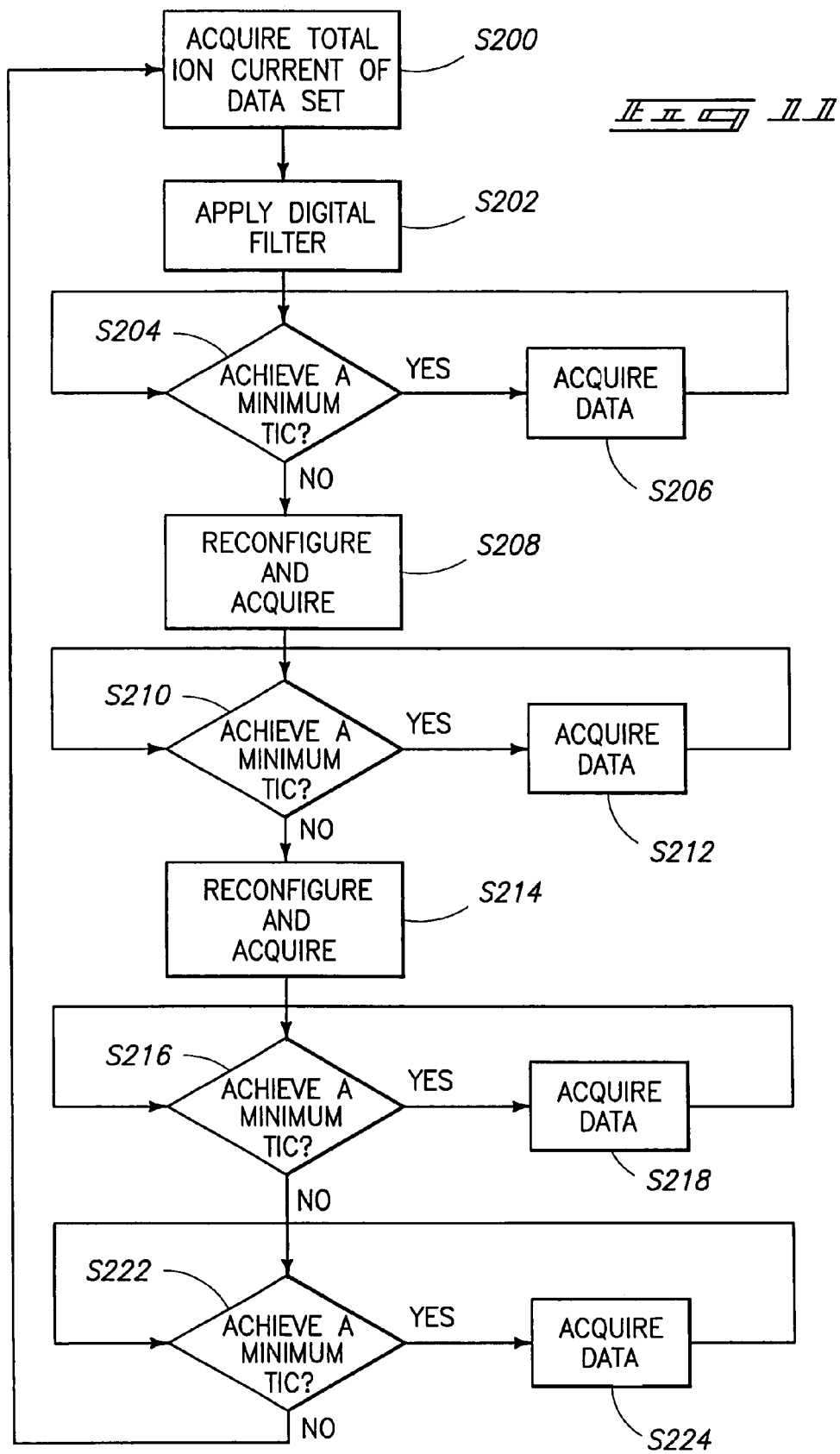

ANALYTICAL INSTRUMENTATION AND SAMPLE ANALYSIS METHODS

RELATED PATENT DATA

This application claims priority to U.S. provisional patent application 60/844,896 which was filed Sep. 14, 2006, entitled "Analytical Instrumentation and Analytical Processes" and which is incorporated by reference herein.

GOVERNMENT RIGHTS STATEMENT

This invention was made with Government support under SBIR Marines Phase III Contract M67004-04-C-0014 awarded by the United States Marine Corps. The Government has certain rights in the invention.

TECHNICAL FIELD

The present disclosure relates to analytical instrumentation and more particularly to sample introduction components of analytical instruments as well as sample analysis methods.

BACKGROUND

Analytical instruments can take many forms and acquire numerous forms of data. For example, acquired data may be quantitative, qualitative, and/or some combination of both quantitative and/or qualitative. Many instruments have limits. These limits include detection limits, the level at which either qualitative or quantitative data can be acquired. Data may be below the detection limit for example. In other examples, the data may be outside the analytical range of the instrument by being beyond the upper limit of the instrument.

In many circumstances, chemistry, in the form of pollutants or even munitions, happens outside the lab, making it difficult for instrument operators to initially configure analytical instruments with an analytical range that will encompass the unknown amounts of analytes within a given sample. A need exists for analytical instruments that dynamically adjust to unknown sample concentrations.

SUMMARY OF THE DISCLOSURE

Sample introduction components of analytical instruments are provided that can include a membrane inlet component in fluid communication with both a mass analyzer component and a sample inlet. The components can also include a valve in fluid communication with the sample inlet and a sampling component.

Sample introduction components of analytical instruments can include a sample loop assembly in fluid communication with valve, and a preconcentration assembly in fluid communication with the valve. The instrument can be configured to receive samples via either the sample loop assembly or the preconcentration assembly.

Sample introduction components of analytical instruments can also include a membrane inlet component in fluid communication with both a mass analyzer component and a sample inlet. The components can include a valve in fluid communication with both the sample inlet and at least one or both of a sampling loop assembly and a preconcentration assembly.

Sample analysis methods are provided that can include providing a sample to a membrane in fluid communication with a mass analyzer to acquire sample parameter data, and providing the sample to a sampling assembly upon acquisition of predefined sample parameter data.

Methods can also include providing a sample to a first sampling assembly in fluid communication with a detection component to acquire sample parameter data, providing the sample to a second sampling assembly upon acquisition of predefined sample parameter data.

DESCRIPTION OF THE DRAWINGS

Embodiments of the disclosure are described below with reference to the following accompanying drawings.

FIG. 10 is a configuration of the component of FIG. 3 according to an embodiment.

FIG. 11 is a process according to an embodiment.

DETAILED DESCRIPTION OF THE PREFERRED EMBODIMENTS

This disclosure is submitted in furtherance of the constitutional purposes of the U.S. Patent Laws "to promote the progress of science and useful arts" (Article 1, Section 8).

Embodiments of the analytical apparatuses, instrumentation and methods are described with reference to FIGS. 1-11.

Figure 1:
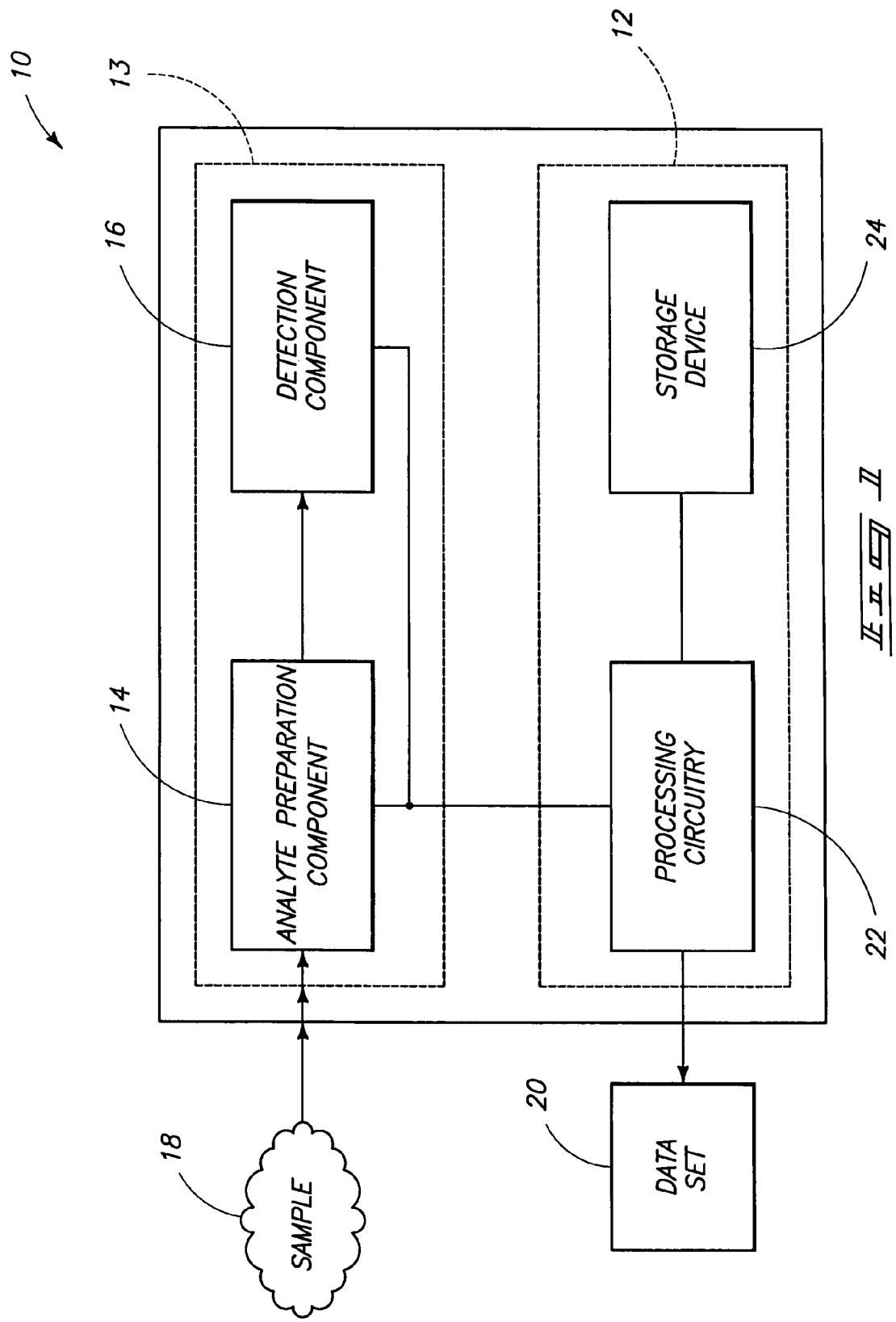
FIG. 1 is an analytical instrument according to an embodiment.

Referring first to FIG. 1, instrument 10 is shown that includes processing and control component 12 coupled to analysis component 13. Instrument 10 can be configured to receive a sample 18 for analysis and provide a data set 20 upon analysis of sample 18, for example.

Analytical instrumentation can include an analyte preparation component and a detection component coupled to a processing and control component. The processing and control component can take the form of a computer that is configured to control analysis by providing parameters to the analyte preparation and/or the detection components. For example, in the case of mass spectrometry instrumentation, the processing and control component may provide a detection parameter to the detection component, such as a voltage to the electron multiplier and/or engagement of the electron multiplier in the on or off stage. Likewise, the processing and control component may also provide analytical preparation component parameters in the form of sampling component parameters. These parameters can be downloaded to these components by the processing and control component and data sets are acquired utilizing these parameters. Upon interpretation of the acquired data sets, the operator of the instrument may feel it is necessary to redefine certain parameters, download these parameters, and acquire additional sets of data.

Sample 18 can be any known and/or unknown chemical composition. For example, sample 18 can be any chemical composition including both inorganic and organic substances in solid, liquid and/or vapor form. Specific examples of sample 18 suitable for analysis in accordance with the present disclosure include volatile compounds, such as toluene, and/or semi-volatile or even non-volatile compounds. In certain aspects, sample 18 can be a mixture containing more than one substance or in other aspects sample 18 can be a substantially pure substance.

Data set 20 can be qualitative and/or quantitative data parameters. For example, a data parameter can include the mass spectra which when interpreted can provide the qualitative identity of an analyte compound within the sample. As another example, a data parameter may include quantitative amounts, such as the total ion current, which can indicate the quantity of single and or multiple analytes within the sample.

Instrument 10 can be any instrument configured with a processing and control component 12 and an analysis component 13. This includes analytical apparatuses used for chemical analysis such gas or liquid chromatographs equipped with detectors such as flame ionization, UV-vis, conductivity, IR, and/or mass spectrometry detectors. Instrument 10 can be configured as described in U.S. patent application Ser. No. 10/542,187, now U.S. Pat. No. 7,427,750 entitled Mass Spectrometer Assemblies, Mass Spectrometry Vacuum Chamber Lid Assemblies, and Mass Spectrometer Operational Methods filed Jul. 13, 2005, the entirety of which is incorporated by reference herein. Instrument 10 can also be configured as described in U.S. patent application Ser. No. 10/554,039, now U.S. Pat. No. 7,462,821 entitled Instrumentation, Articles of Manufacture, and Analysis Methods, filed Oct. 20, 2005, the entirety of which is incorporated by reference herein. As another example, instrument 10 can be configured as described in International Patent Application Serial No. PCT/US05/20783 entitled Analytical Instruments, Assemblies, and Methods, filed Jun. 13, 2005, the entirety of which is incorporated by reference herein. Analysis component 13 is coupled to a processing and control component 12.

Analysis component 13 can include a detection component 16 coupled to processing and control component 12 as well as analyte preparation component 14. Detection component 16 can include a mass spectrometer, a flame ionization detector, a thermal conductivity detector, a thermal ionic detector, an electron capture detector, or an atomic emission detector. Furthermore, detection component 16 can include an absorbance detector such as an ultraviolet absorbance detector, a fluorescence detector, an electrochemical detector, a refractive index detector, a conductivity detector, a fourier transform infrared spectrometer, a light scattering detector, a photo ionization detector, and/or a diode array detector. Detection component 16 can be an atomic spectroscopy detector, an emission spectroscopy detector, or a nuclear magnetic resonance spectroscopy detector. Exemplary detection components include those described in U.S. patent application Ser. No. 10/537,019 now U.S. Pat. No. 7,294,832 entitled Mass Separators filed Jun. 1, 2005, the entirety of which is incorporated by reference herein. Additional detection components include those described in International Patent Serial No. PCT/US04/29127 entitled Ion Detection Methods, Mass Spectrometry Analysis Methods, and Mass Spectrometry Instrument Circuitry, filed Sep. 3, 2004, the entirety of which is incorporated by reference herein.

Analyte preparation component 14 can be configured according to analysis parameters including sets of parameters. The control of sampling, such as sampling times, types of sampling techniques, and/or sampling assembly selection can be parameters of the analysis parameter sets. As an example, detection component 14 can be a mass spectrometry inlet component that includes a sampling assembly defined by the analysis parameter set and coupled to a mass analyzer and detection components. The sampling assembly can be configured according to a sampling component parameter set of the analysis parameter set that can include, for example, sampling assembly parameters. The configuration of component 14 according to analysis parameter sets for the analysis of sample 18 can affect what is acquired in the form of data set 20. For example, in the case of sampling components, selection of sampling assemblies as dictated by sampling apparatus parameter sets can significantly enhance the sensitivity of instrument 10, and/or bring data that under one set of parameters was outside the detection limits of the instrument within a detection range.

Analysis component 13 can also include detection component 16 that can be configured according to analysis parameter sets such as that described in International Patent Serial No. PCT/US06/15948 entitled Analytical Instrumentation, Apparatuses, and Methods, filed Apr. 25, 2006, the entirety of which is incorporated by reference herein. According to exemplary embodiments, instrument 10 can be configured as described in U.S. patent application Ser. No. 10/570,706, now abandoned, entitled Analysis Device Operational Methods and Analysis Device Programming Methods, filed Mar. 3, 2006, the entirety of which is incorporated by reference herein. Instrument 10 may also be configured as described in U.S. patent application Ser. No. 10/570,707 entitled Analysis Methods, Analysis Device Waveform Generation Methods, Analysis Devices, and Articles of Manufacture, filed Mar. 3, 2006, the entirety of which is incorporated by reference herein.

Processing and control component 12 can be used to configure component 14 according to analysis parameter sets as well as acquire and/or process data set 20. For example data parameters of data set 20 acquired using an analysis component configured as a high performance liquid chromatograph coupled to a diode-array detector can include total absorbance, total absorbance at a selected wavelength, and/or absorbance during a selected time or time range. As another example, data parameters of data set 20 acquired using an analysis component configured as mass spectrometer can include total analyte ion abundance and/or total abundance at a specified m/z ratio. Component 12 can be configured to process data and select analysis parameters based on the data acquired. Where acquired data is below detection limits, component 12 can be configured to select an analysis parameter that can include a sampling apparatus parameter other than the sampling apparatus parameter used to acquire the data. As an example, to acquire the data, a sampling loop was utilized, and upon determination of below detection limits, component 12 reconfigures the instrument to utilize a preconcentration sampling assembly to acquire the next set of data.

Processing and control component 12 can be a computer and/or mini-computer capable of controlling the various parameters of instrument 10. Processing and control component 12 can include processing circuitry 22 and storage device 24. Processing circuitry 22 is configured to acquire analytical component parameters from storage device 24 as well as acquire process data set 20 received from detection component 16, for example. Circuitry 22 is also configured to process data set 20 received from detection component 16 and dynamically modify parameters of component 14. The modification of the parameters of component 14 can take place while instrument 10 is analyzing sample 18 and/or in between analyses of sample 18 utilizing instrument 10, for example.

Acquisition and generation of data according to the present disclosure can be facilitated with processing and control component 12. This control includes the specific application of sampling component parameter sets including selection of sampling assemblies and parameters for use with these sampling assemblies. Processing and control component 12 can contain data acquisition and searching software. In one aspect such data acquisition and searching software can be configured to perform data acquisition and searching that includes the programmed acquisition of data parameter such as the total analyte count described above. In another aspect, data acquisition and searching parameters can include methods for correlating the amount of analytes generated to predetermined programs for acquiring data.

Processing circuitry 22 may be implemented as a processor or other structure configured to execute executable instructions including, for example, software and/or firmware instructions. Processing circuitry 22 may additionally include hardware logic, PGA, FPGA, ASIC, and/or other structures. In exemplary embodiments, data set 20 may be output from instrument 10 via FPGA processing circuitry 22. In another embodiment, data set 20 may be directly output from a bus of processing circuitry 22 where an appropriate bus feed is provided. Processing circuitry 22 may include an analog to digital converter (ADC) to retrieve, record, and/or convert data set 20 during analog processing utilizing processing circuitry 22. Processing circuitry 22 may also amplify analog signals received from detection component 16 before processing data set 20.

Storage device 24 is coupled to processing circuitry 22 and is configured to store electronic data, programming, such as executable instructions (e.g., software and/or firmware), data, or other digital information that may include processor usable media. Processor usable media includes any article of manufacture which can contain, store, or maintain programming data or digital information for use by, or in connection with, an instruction execution system including processing circuitry in the exemplary embodiment. Storage device 24 can house multiple analysis parameter sets as well as multiple data analysis parameter sets.

Exemplary processor usable media may include any one of physical media such as electronic, magnetic, optical, electromagnetic, infrared or semiconductor media. Some more specific examples of processor usable media include, but are not limited to, a portable magnetic computer diskette, such as a floppy diskette, zip disk, hard drive, random access memory, read only memory, flash memory, cache memory, and/or other configurations capable of storing programming, data, or other digital information.

Processing and control component 12, including processing circuitry 22 in combination with storage device 24, may be utilized to modify parameters of component 14 by processing data set 20 in the context of the analysis component parameters used to generate data set 20. For example, data set 20 can include parameters of the data set, such as total analyte ion abundance in the case of a mass spectrometry instrument data set. The total abundance can be processed in the context of the component 14 parameters used to generate the data set parameter, such as a sampling media parameter of a sampling apparatus component. Upon processing data set 20 in the context of the analysis component parameters used to generate data set 20, the component parameters may be modified, component 14 can be reconfigured with the modified parameters, and a subsequent analysis of sample 18 performed using instrument 10 as reconfigured. This analysis may be utilized continuously or intermittently as the user of instrument 10 dictates.

Figure 2:
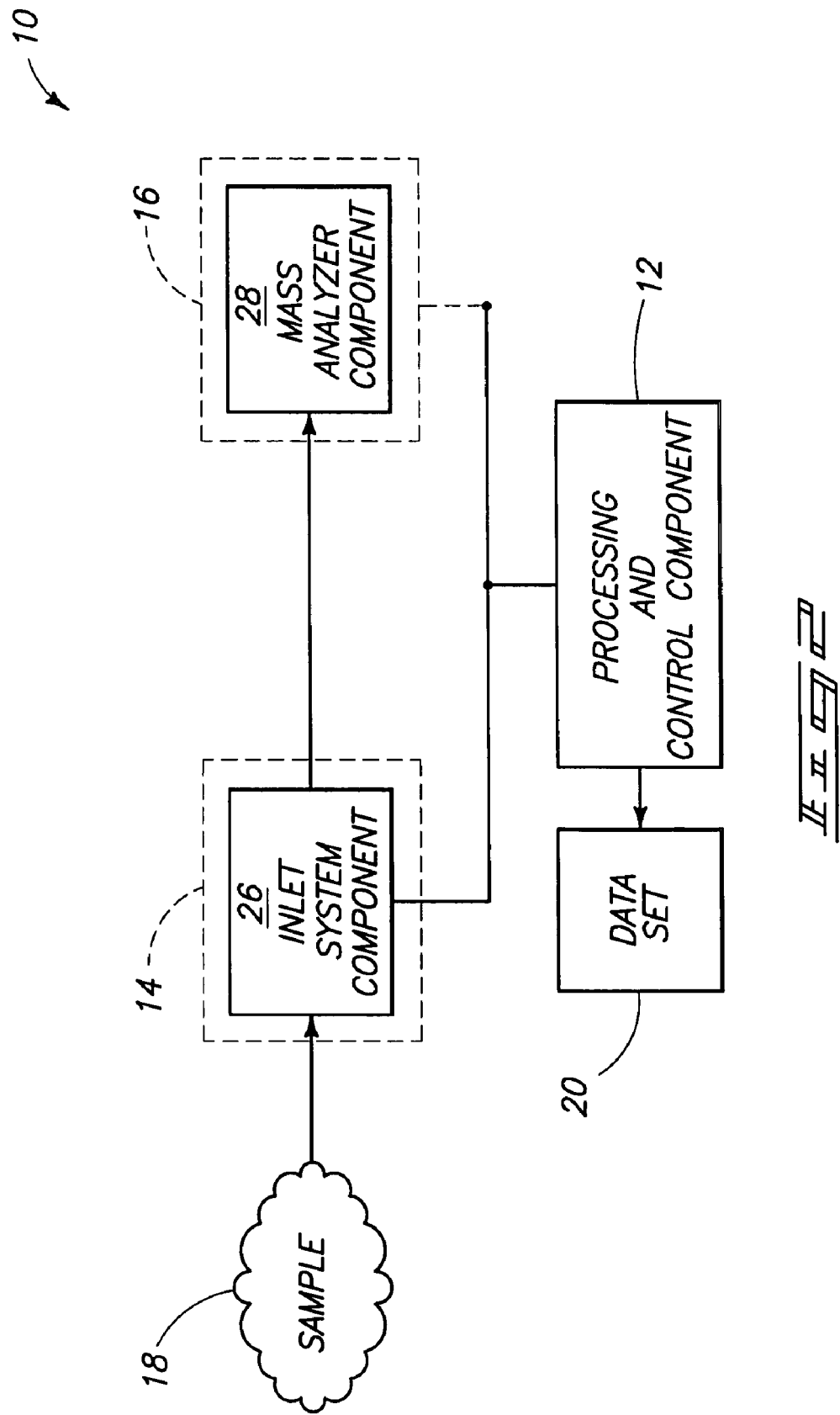
FIG. 2 is one embodiment of a mass spectrometry instrument according to an aspect of the present disclosure.

According to an exemplary embodiment reference is made to FIG. 2, where a block diagram of instrument 10 is shown configured as a mass spectrometry instrument to include an inlet system component 26 and mass analyzer component 28, all in connection with a processing and control component 12. As depicted in FIG. 2, a sample 18 can be introduced into inlet system component 26. Analysis of sample 18 will now be described with reference to aspects of the present disclosure in an effort to provide further exemplary embodiments.

Figure 3:
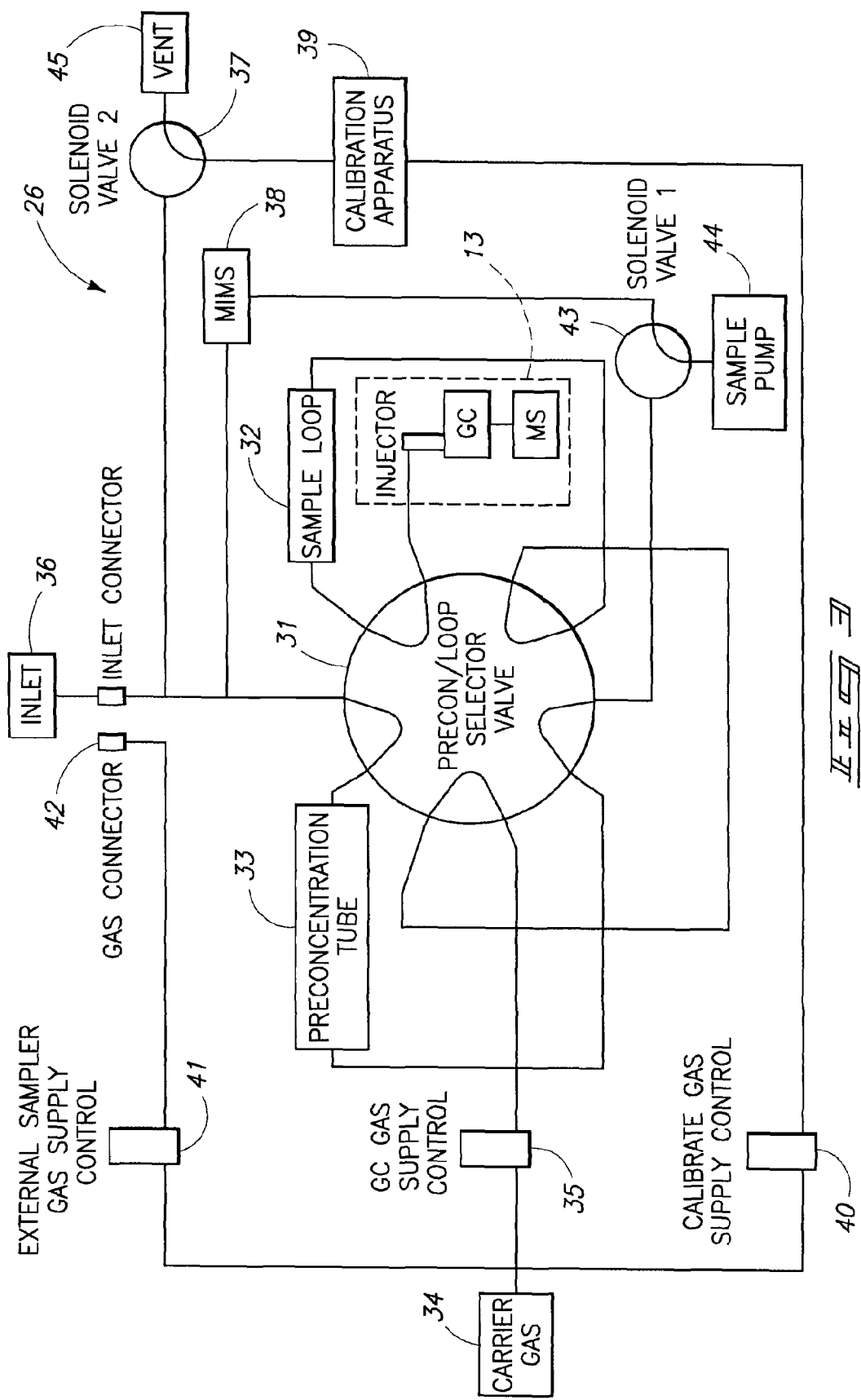
FIG. 3 is an embodiment of a component of an analytical instrument according to an aspect of the present disclosure.

Referring to FIG. 3, inlet system component 26 such as a sample introduction component can be configured to introduce an amount of sample 18 into instrument 10. Component 26 may be configured to prepare sample 18 for analysis in the gas, liquid and/or solid phase. Component 26 may be configured around a selector valve 31 such as a two-position valve that may be operated between the two positions mechanically. Valve 31 can be coupled to a motor (not shown) which can be controlled by component 12, for example. Valve 31 can be in fluid communication with inlet 36 as well as fluid communication with at least one sampling assembly or component 32, such as a sample loop. Sample loops are available in volumetric sizes and may be selected as the instrument user dictates. Valve 31 may also be in fluid communication with another sampling assembly or component 33, such as a pre-concentrating apparatus or preconcentration assembly, including tubes housing solid phase media configured to facilitate the adsorption of some substances to the exclusion of other substances. Valve 31 may also be coupled to a mobile phase, such as GC gas supply 34 via gas supply control 35. Valve 31 is also coupled to the remainder of component 13, such as a gas chromatograph and mass spectrometer.

According to exemplary embodiments, component 26 can include an inlet 36 that is coupled to both valve 31, another valve 37, and a membrane inlet component 38, such as a membrane utilized to facilitate membrane introduction mass spectrometry (MIMS). Component 38 can include a membrane separating sample from a mass analyzer, with the membrane being configured to allow analytes of the sample to permeate and proceed to the mass analyzer to the exclusion of other components of the sample. Component 38 can be in fluid communication with inlet 36 as well as a mass analyzer.

Inlet 36 can be selectively coupled to these valves using other valves (not shown). Valve 37 can be coupled to a vent 45 as well as a calibration apparatus 39 which can also be coupled to a calibrant gas supply control 40. Calibration apparatus 39 can take the form of a permeation source and can be configured to be a source of known compound that generates a known data set, for example a known mass spectrum. Apparatus 39 may also take the form of single or multiple containers containing standards that are coupled to component 26 and more particularly valve 31. Control 40 can be coupled to gas connector 42 via external sampler gas supply control 41. Membrane 38 can be coupled to valve 31 via valve 43. Valve 43 can also be coupled to a sample pump 44.

In accordance with a calibration set of parameters, carrier gas can be supplied to calibration apparatus 39 of calibrant to facilitate calibration of the instrument. When supplied to calibration apparatus 39, the flow stream from the calibration apparatus can be directed to the inlet line via valve 37. Accordingly, quantitative and/or qualitative (i.e. mass spectral m/z assignment) calibration of instrument 10 can be accomplished. According to example implementations, instrument 10 can be calibrated while acquiring sample for analysis.

Figure 4:
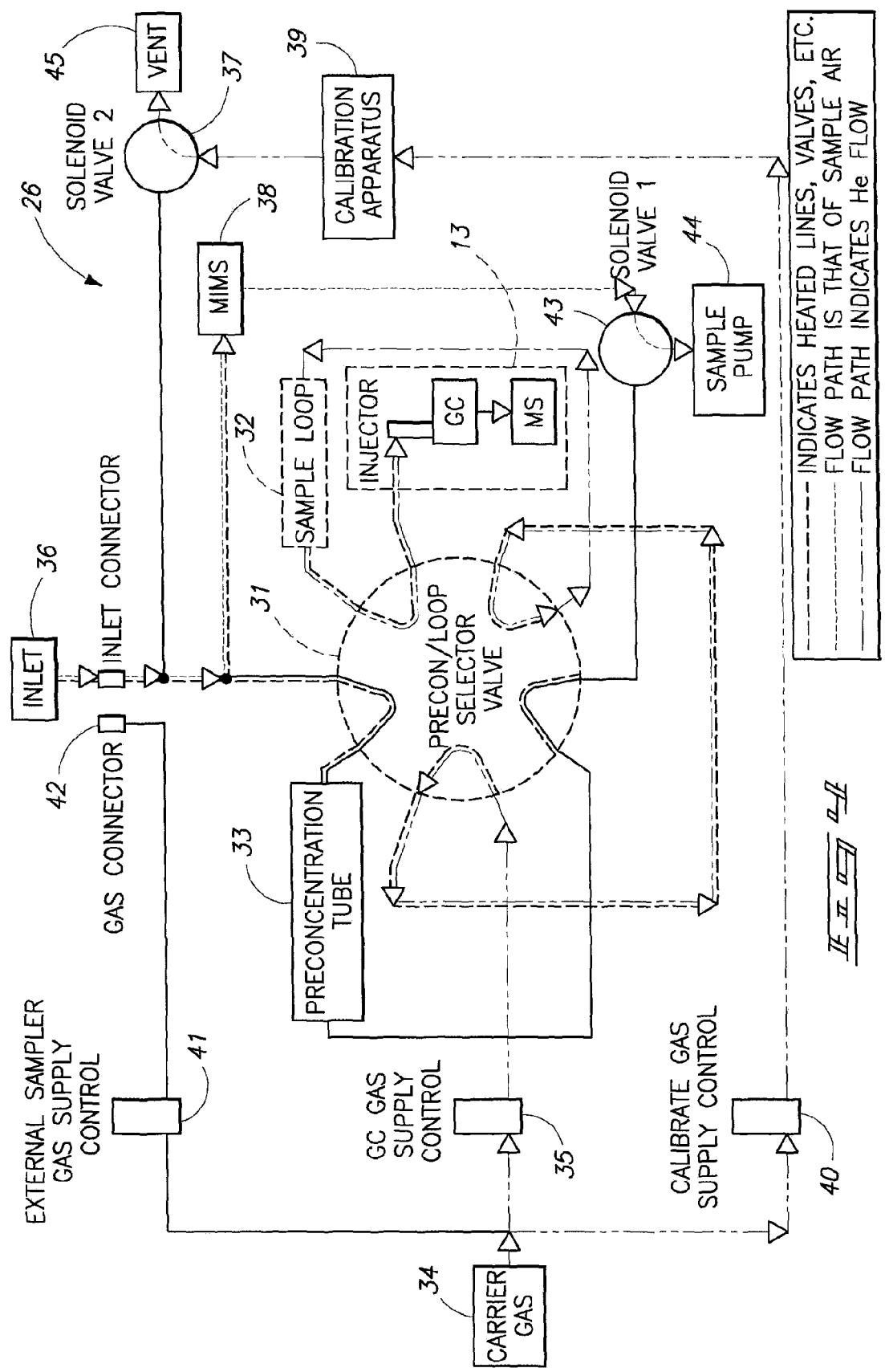
FIG. 4 is a configuration of the component of FIG. 3 according to an embodiment.

In accordance with one set of sampling parameters, component 26 can be configured to utilize MIMS either in real time or as dictated by the sampling parameters. With reference to FIG. 4, a sampling parameter set may dictate that sample pump 44 is activated to move sample air from the inlet through membrane 38, through valve 43. During this time target analytes can pervaporate across the membrane in real- or near-real-time into the mass spectrometer vacuum system where they are analyzed and a data set acquired. This configuration can be used for relatively high concentrations of analytes. Valve 31 can be configured to connect assembly 32 with component 13 to provide carrier gas (aka, mobile phase). In this example configuration the sampling introduction component can be configured to receive the sample and provide the sample to the instrument via the membrane inlet. While acquiring data using MIMS, component 26 may also provide calibrant from apparatus 39 to the detection component. In this implementation, instrument 10 may be calibrated utilizing a spiked sample technique, for example.

MIMS system can also be configured for trap-and-release mode and accordingly sample can be flushed through the membrane as in the pervaporation method. During this sample flow, analyte can adsorb to the membrane and preconcentrate. After a predetermined sampling time parameter has been achieved, pump 44 can be turned off and membrane 38 heated to release the trapped analyte into component 13 for data acquisition. Upon acquisition of data with component 26 in this configuration, component 12 can reconfigure component 26 to acquire data using another configuration, such as those shown in FIGS. 5-8. This reconfiguration can be programmed to occur upon the acquisition of predefined sample parameter data, for example, such as a total ion current. For example a threshold total ion current can be designated and upon acquiring data above the threshold, component 12 can reconfigure the instrument to provide sample to an alternative sampling assembly or assemblies. As another example, specific mass/charge ratios and/or a range of mass/charge ratios can be designated and upon recording the specific mass/charge ratios or mass/charge ratios within the range, component 12 can reconfigure to provide sample to an alternative sampling assembly or assemblies.

Figure 5:
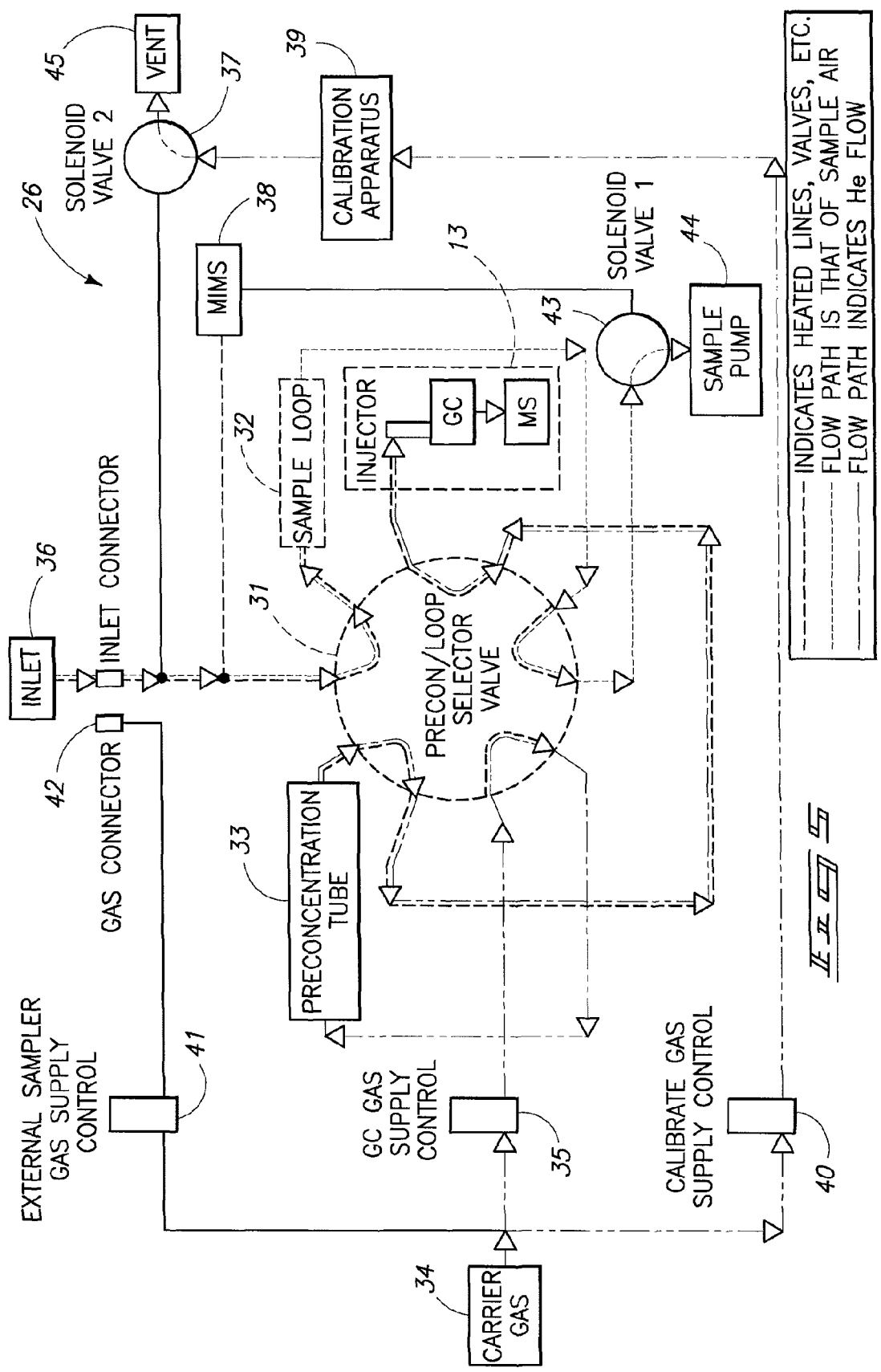
FIG. 5 is a configuration of the component of FIG. 3 according to an embodiment.

According to another set of parameters, component 26 can be configured to fill assembly 32. Referring to FIG. 5, valves 31 and 43 are configured to allow pump 44 to move sample air through loop 32. Valve 31 is configured to direct carrier gas through assembly 33 to component 13. In addition, carrier gas can be supplied to calibration apparatus 39. In this example configuration sample introduction component 26 can be configured to provide sample to the instrument via the sampling component in another configuration other than the MIMS configuration described above, for example. In accordance with an example implementation, while assembly 32 is being provided with sample, component 26 can be configured to provide calibrant from apparatus 39 to instrument 10 for calibration of the instrument.

Figure 6:
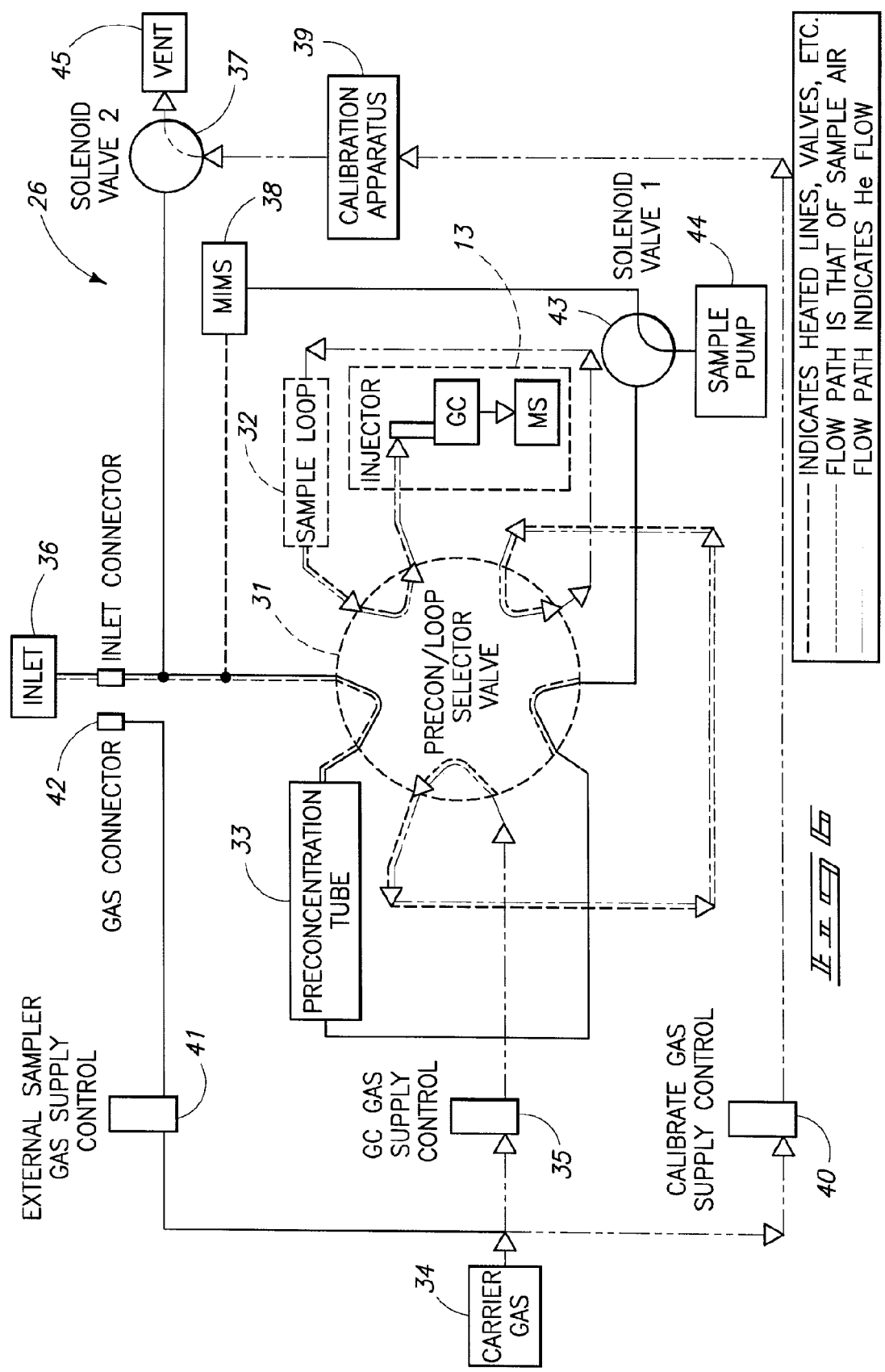
FIG. 6 is a configuration of the component of FIG. 3 according to an embodiment.

Referring to FIG. 6, component 26 can be configured to provide the contents of assembly 32 to component 13. According to exemplary embodiments, pump 44 is turned off and valve 31 is configured to direct carrier gas through assembly 32 and provide its contents to component 13. In this configuration another sample parameter data set may be acquired and processed. The processing may dictate the reconfiguration of the instrument to alternative sampling parameter sets.

Figure 7:
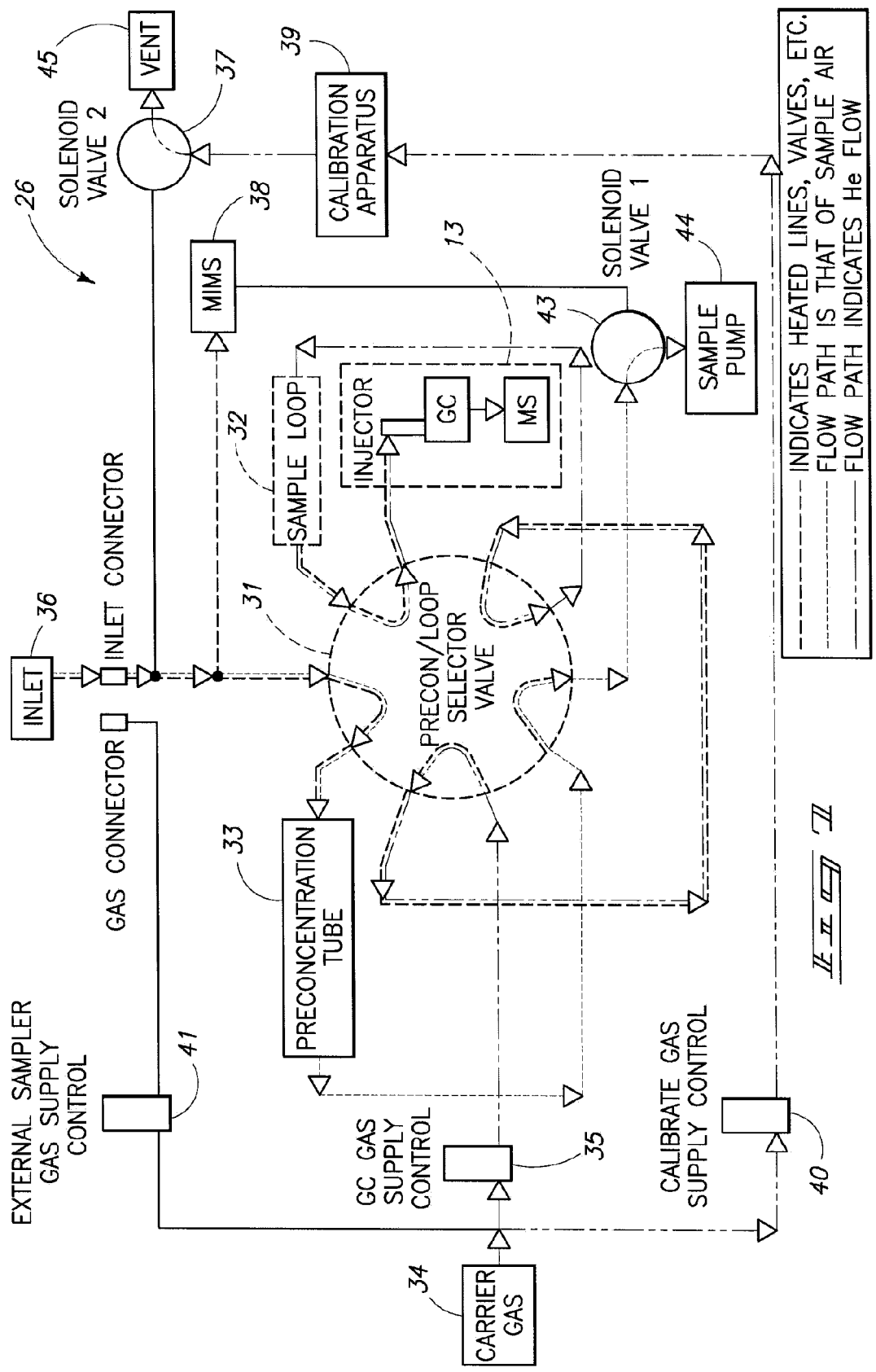
FIG. 7 is a configuration of the component of FIG. 3 according to an embodiment.

According to still another set of parameters, component 26 can be configured to sample via a preconcentration assembly such as a preconcentration tube. Referring to FIG. 7, sample pump 44 can be turned on, valve 43 and valve 31 can be set to direct sample air through assembly 33 while carrier gas flows through assembly 32 to maintain flow into component 13.

Figure 8:
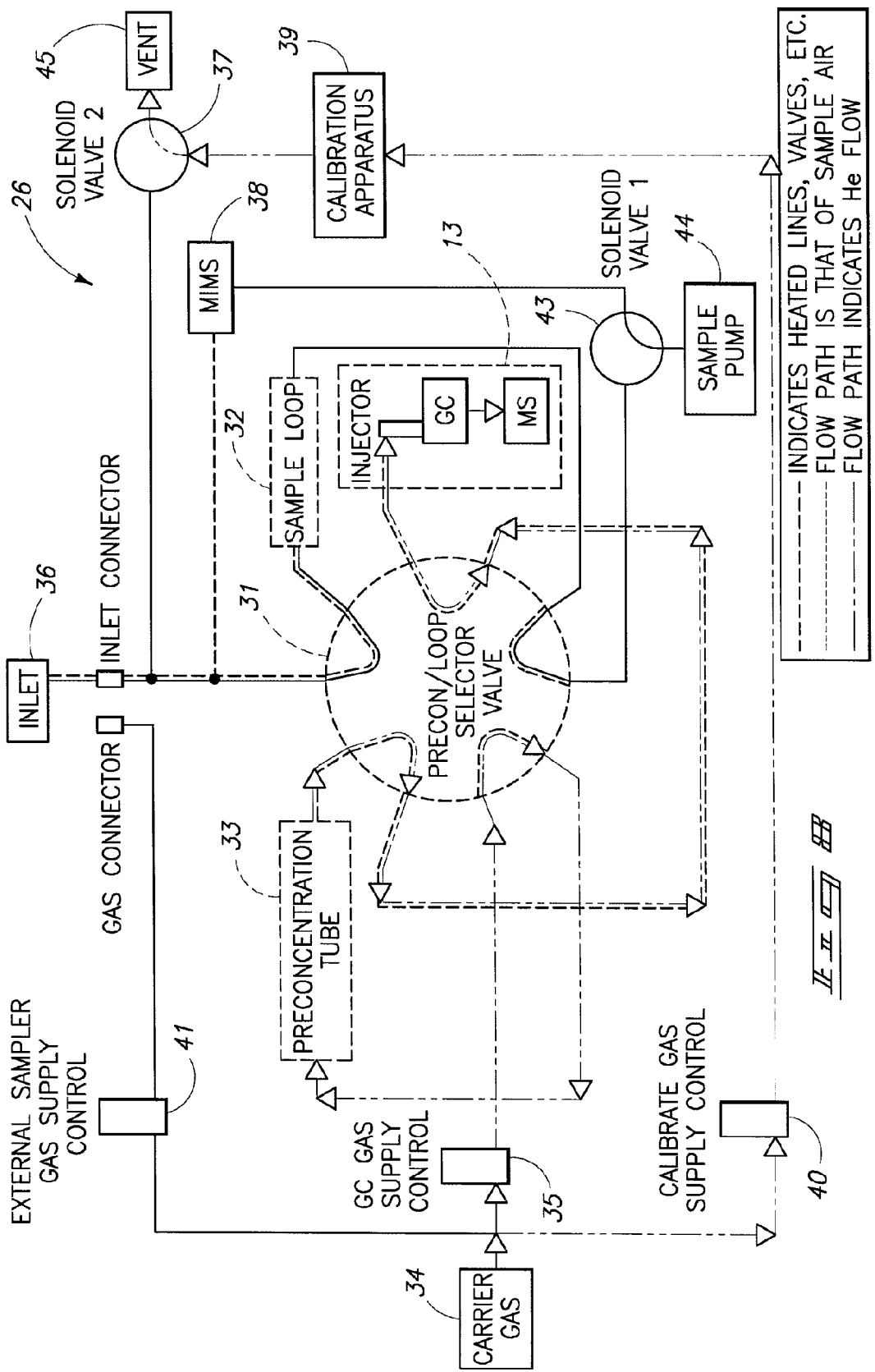
FIG. 8 is a configuration of the component of FIG. 3 according to an embodiment.

Carrier gas can also be supplied to calibration apparatus 39 to simultaneously calibrate instrument 10 while gathering sample within assembly 33. Referring to FIG. 8, tube 33 can be desorbed and the contents provided to component 13 via another set of sampling parameters. Accordingly, pump 44 and valve 43 are turned off while valve 31 is switched to direct carrier gas through assembly 33 (e.g., in the direction opposite the sampling flow) to component 13. During this time assembly 33 can be rapidly heated to release trapped analyte for subsequent analysis such as gas chromatography utilizing component 13. Carrier gas can also be supplied to calibration apparatus 39. In this configuration another sample parameter data set may be acquired and processed. The processing may dictate the reconfiguration of the instrument to alternative sampling parameter sets.

Accordingly, sample analysis methods can include providing sample to a first sampling assembly, for example MIMS, assembly 32 or assembly 33 which can be in fluid communication with a detection component to acquire a sample parameter data set. Upon processing data with component 12, for example, component 26 can be reconfigured to provide sample to a second sampling assembly upon acquisition of predefined sample parameter data sets. The first sampling assembly can be different from the second sampling assembly. The sampling assemblies may also be the same but the sampling parameters may be different. For example, MIMS may be utilized to acquire Total Ion Current in one parameter set and specific mass/charge ratios in another parameter set.

Figure 9:
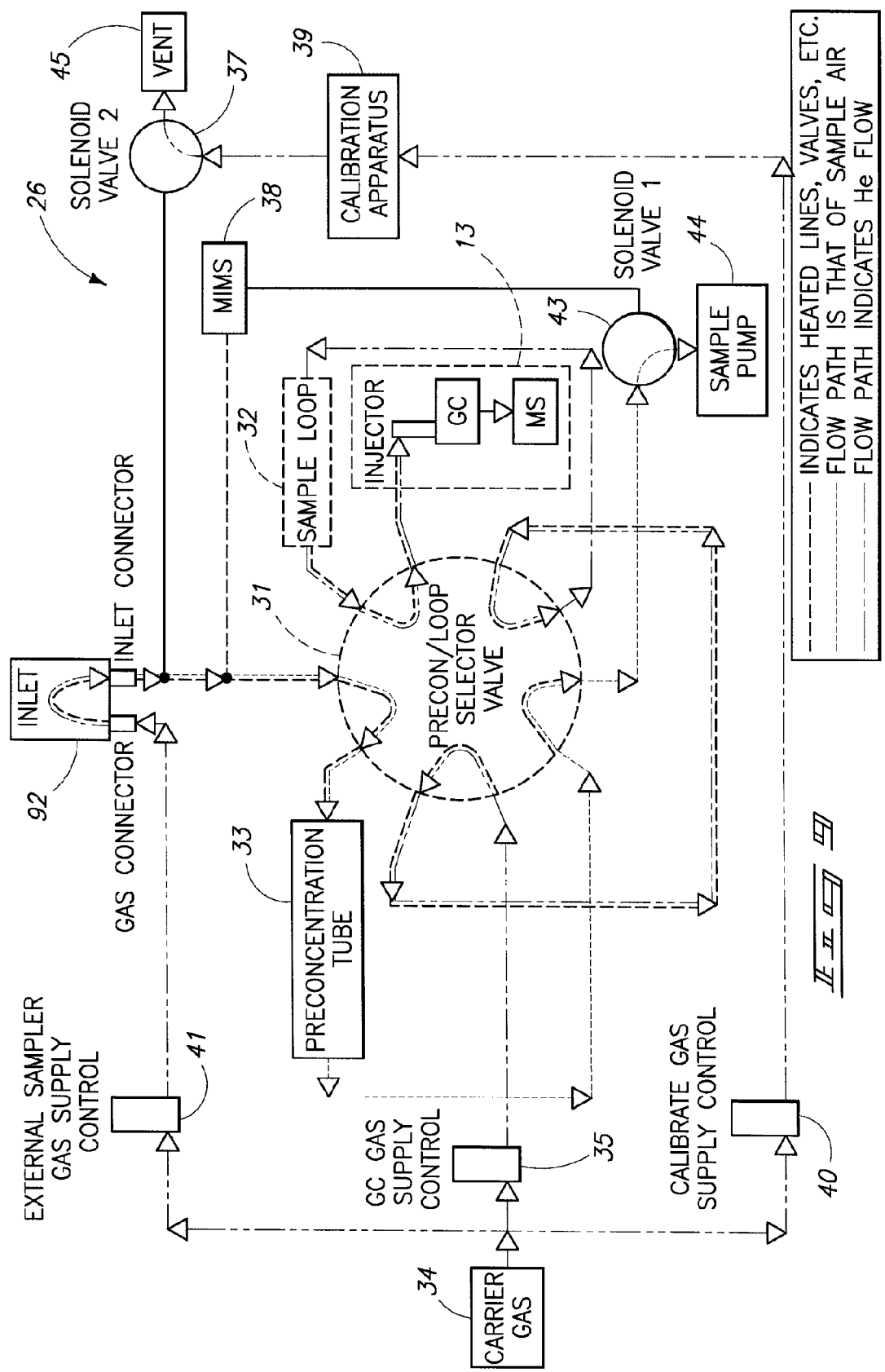
FIG. 9 is a configuration of the component of FIG. 3 according to an embodiment.

In accordance with yet another set of sample parameters, component 26, when coupled to an external sampler, can be configured to transfer the sample of the external sampler to component 26 and then component 13. This external sampler can be the Griffin X-sorber, manufactured and distributed by Griffin Analytical Technologies, 3000 Kent Avenue, West Lafayette, Ind. 47906. The external sampling device can be configured to be removably coupled to component 26 and/or instrument 10. When coupled with instrument 10, the sampling device can also couple with component 12. Referring to FIG. 9, the carrier gas can be directed via control 41 to flow through an external sampler 92 that has been connected to inlet 36 and connector 42. During this time a preconcentration tube of sampler 92 can be heated to release trapped sample that is then recollected within assembly 33. Component 26 can be configured to receive the sample from an external sampling device with the assembly 33 being configured to receive the sample and valve 31 being configured to allow fluid communication between assembly 33 and assembly 32. The carrier gas can be vented through sample pump 44. Additional carrier gas can be directed to component 13 via loop 32 and carrier gas can be supplied to calibration apparatus 39.

Referring to FIG. 10, component 26 can be configured according to another set of sampling parameters to provide the contents of assembly 33 to component 13 when component 26 is coupled to sampler 92. Accordingly, component 26 is configured as described in FIG. 8 above to desorb trapped sample into component 13. In addition, carrier gas is supplied to the calibration apparatus 39.

According to exemplary embodiments, component 13 can include an ion source component that can be configured to receive sample 18 from component 26 and convert components of sample 18 into analyte ions. The ion source may utilize electron ionization (EI, typically suitable for the gas phase ionization), photo ionization (PI), chemical ionization (CI), and/or collisionally activated disassociation. For example in PI, the photon energy can be varied to vary the internal energy of the sample. The ion source can be configured to generate an analyte beam that may be provided to a mass analyzer component 28 and subjected to further manipulations known in the art, for example, mass analysis, and/or tandem mass spectrometry to acquire data set 20 for processing by processing and control component 12.

Mass analyzer component 28 can include magnetic sectors, electrostatic sectors, and/or quadrupole filter sectors. More particularly, mass analyzer component 28 can include one or more of triple quadrupoles, quadrupole ion traps, cylindrical ion traps, linear ion traps, rectilinear ion traps, ion cyclotron resonance and quadrupole ion trap/time-of-flight mass spectrometers. Quadrupole ion traps or "Paul traps" can refer to an ion trap having a toroidal ring electrode and two end caps. The toroidal ring electrode may have a hyperbolic shape in one cross section. The two end caps may also have a hyperbolic shape in one cross section. Cylindrical ion traps (CIT) have been considered a variation on the quadrupole ion trap where the ring electrode and end caps may have flat surfaces in one cross section. Linear ion traps can consist of sets of parallel rods, the rods being either round, hyperbolic, and/or flat in one cross section.

Mass analyzer component 28 can include or be coupled to a detection component. Exemplary detection components can include one or more of electron multipliers, Faraday cup collectors, and photographic detectors. Detection components can yield a signal which is proportional to the total number of analytes being generated by the ion source component over time. The total number of analyte ions being generated over time can be referred to as a total analyte ion count and/or total analyte ion abundance. It is understood that the total analyte ion abundance can vary depending on the characteristics of sample 18, and the configuration of component 26. By processing data set 20 acquired using analysis component 26 configured with analysis parameter sets as described, automated sampling to acquire data having varying degrees of sensitivity can be accomplished. For example, sampling component parameter sets such as: MIMS sampling; loop sampling; and tube sampling can be defined according to the component configurations described above with reference to FIGS. 4-8. Each of these configurations can be represented by the sampling parameters necessary to configure component 26 to sample accordingly.

Referring to FIG. 11, an exemplary process is provided for determining if the configuration of component 26 should be modified and modifying sampling parameter sets to reconfigure component 26 when a determination of modification is made. Referring to FIG. 11, for example, the process begins with S200 where the total ion current parameter of a data set is acquired and the process proceeds to applying a digital filter to this data set parameter at S202. According to exemplary embodiments, to acquire the total ion current data, component 26 can be configured according to the MIMS configuration. Exemplary filters include a two pole Butterworth algorithm but other filters and/or no filter can also be used. From there the process proceeds to S204 where a determination is made as to whether the total ion current has achieved a minimum TIC as dictated by the instrument operator. Where it has exceeded the minimum TIC, data is acquired using the MIMS configuration in S206.

Where a minimum TIC is not achieved as calculated in S204, the process proceeds to S208 where component 26 is reconfigured to sample in the Loop Sampling configuration, for example, and acquire data. At S210 determination is made as to whether or not the total ion current has achieved a minimum threshold amount, the amount can be less than the threshold amount of S204. Where the threshold amount has been achieved, the process continues to S212 and data is acquired using component 26 configured with loop sampling parameters.

Where a minimum TIC is not achieved as calculated in S210, the process proceeds to S214 where component 26 is reconfigured to sample in the Tube Sampling configuration, for example, and acquire data. At S216 a determination is made as to whether or not the total ion current has achieved a minimum threshold amount; the amount can be less than the threshold amount of S210. Where the threshold amount has been achieved, the process continues to S218 and data is acquired using component 26 configured with Tube Sampling parameters. Where the minimum threshold has not be achieved in S216, the process can return to S200.

Upon acquiring data at S206, S212, and/or S218, instrument 10 can be configured to acquire additional sample for analysis. This additional sample can be analyzed and the method utilized to determine predefined threshold data parameters utilizing S204, S210, and/or S216 respectively. According to an example implementation, upon not achieving a minimum threshold value of a data set parameter, such as a minimum TIC, after S222, the instrument can be configured to reconfigure and acquire data using the same assemblies, but with different sampling parameters. For example, upon not acquiring a minimum TIC in S204, S210, S216, or S220, the instrument can be reconfigured to extend the time sample is passed through a sampling assembly such as a preconcentration assembly, these sampling parameters can be dynamically adjusted as the user desires and/or as the hardware allows.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A sample analysis method comprising:
providing sample to a first sampling assembly in fluid communication with a detection component to acquire sample parameter data, wherein the first sampling assembly is a sample loop; and
providing the sample to a second sampling assembly upon acquisition of sample parameter data below a detection limit.

2. The method of claim 1 wherein the second sampling assembly is a preconcentration assembly.

3. A sample analysis method comprising:
providing sample to a first sampling assembly in fluid communication with a detection component to acquire sample parameter data, wherein the first sampling assembly is a preconcentration assembly; and
providing the sample to a second sampling assembly upon acquisition of sample parameter data above an upper detection limit.

* * * * *

UNITED STATES PATENT AND TRADEMARK OFFICE
CERTIFICATE OF CORRECTION

PATENT NO. : 7,992,424 B1  Page 1 of 1
APPLICATION NO. : 11/900958
DATED : August 9, 2011
INVENTOR(S) : John W. Grossenbacher It is certified that error appears in the above-identified patent and that said Letters Patent is hereby corrected as shown below:

Column 10, line 16 – Replace "not be" with --not been--

Signed and Sealed this
Twentieth Day of December, 2011

David J. Kappos
*Director of the United States Patent and Trademark Office*